US010532969B2

(12) United States Patent
Shi et al.

(10) Patent No.: US 10,532,969 B2
(45) Date of Patent: Jan. 14, 2020

(54) METHOD FOR DIRECTLY PREPARING GLYCOL DIMETHYL ETHER AND CO-PRODUCING ETHYLENE GLYCOL FROM ETHYLENE GLYCOL MONOMETHYL ETHER

(71) Applicant: Dalian Institute of Chemical Physics, Chinese Academy of Sciences, Dalian (CN)

(72) Inventors: Lei Shi, Dalian (CN); Youming Ni, Dalian (CN); Wenliang Zhu, Dalian (CN); Yong Liu, Dalian (CN); Hongchao Liu, Dalian (CN); Zhongmin Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 15/763,318

(22) PCT Filed: Dec. 11, 2015

(86) PCT No.: PCT/CN2015/097160
§ 371 (c)(1),
(2) Date: Mar. 26, 2018

(87) PCT Pub. No.: WO2017/054321
PCT Pub. Date: Apr. 6, 2017

(65) Prior Publication Data
US 2018/0273455 A1 Sep. 27, 2018

(30) Foreign Application Priority Data

Sep. 30, 2015 (CN) .......................... 2015 1 0639716

(51) Int. Cl.
C07C 41/14 (2006.01)
C07C 29/128 (2006.01)
B01J 29/08 (2006.01)
B01J 29/18 (2006.01)
B01J 29/40 (2006.01)
B01J 29/65 (2006.01)
B01J 29/78 (2006.01)

(52) U.S. Cl.
CPC ............. *C07C 41/14* (2013.01); *B01J 29/084* (2013.01); *B01J 29/18* (2013.01); *B01J 29/40* (2013.01); *B01J 29/65* (2013.01); *B01J 29/7815* (2013.01); *C07C 29/128* (2013.01); *Y02P 20/52* (2015.11)

(58) Field of Classification Search
CPC ...... B01J 29/7815; C07C 29/10; C07C 41/14; C07C 41/01; C07C 29/128; Y02P 20/52
See application file for complete search history.

(56) References Cited

U.S. PATENT DOCUMENTS 4,579,980 A  4/1986 Kogoma et al.
2001/0007047 A1* 7/2001 Onda ...................... C07C 41/06
568/697
2004/0044253 A1  3/2004 Baimbridge et al.

FOREIGN PATENT DOCUMENTS

| CN | 1184461 A | 6/1998 | |
|---|---|---|---|
| CN | 1762947 A | 4/2006 | |
| CN | 104250206 A | * 12/2014 | ............. C07C 41/09 |
| JP | 60-120829 A | 6/1985 | |
| JP | 60120829 | * 6/1985 | ............. C07C 43/10 |
| WO | 2017/054321 A1 | 4/2017 | |

OTHER PUBLICATIONS

Payra et al. ("Zeolites: A Primer", Marcel Dekker, Inc., 2003, pp. 1-19).*
International Search Report for International Application No. PCT/CN2015/097160, dated Apr. 6, 2017.
Written Opinion of the International Searching Authority for International Application No. PCT/CN2015/097160, dated Apr. 6, 2017.
International Preliminary Report on Patentability for International Application No. PCT/CN2015/097160, dated Apr. 3, 2018.
Supplementary European Search Report for European Application No. EP 15 90 5232, dated Jul. 24, 2018.
Search Report for Chinese Application No. 2015106397160, dated Aug. 22, 2018.
Office Action for Chinese Application No. 2015106397160, dated Sep. 3, 2018.
Zhu, Xinbao et al., "Synthesis and Application of Diethylene Glycol Dimethyl Ether", Jiangsu Chemical Industry, Aug. 2001, pp. 38 to 41, vol. 29, No 4.

* cited by examiner

*Primary Examiner* — Rosalynd A Keys
(74) *Attorney, Agent, or Firm* — Edwin A. Sisson, Attorney at Law, LLC; Jeffrey J. Banyas

(57) ABSTRACT

The present invention provides a method for directly preparing glycol dimethyl ether and co-producing ethylene glycol from ethylene glycol monomethyl ether. More specifically, the method comprises passing a feedstock containing a raw material of ethylene glycol monomethyl ether and a carrier gas through a reactor loaded with a solid acid catalyst to produce glycol dimethyl ether and ethylene glycol, at a reaction temperature range from 40° C. to 150° C. and a reaction pressure range from 0.1 MPa to 15.0 MPa; wherein a carrier gas is an optional inactive gas; and the feedstock contains water whose volume concentration in the feedstock is in a range from 0% to 95%; and the weight hourly space velocity of the raw material of ethylene glycol monomethyl ether is in a range from 0.05 $h^{-1}$ to 5.0 $h^{-1}$; and the volume concentration of the raw material of ethylene glycol monomethyl ether in the feedstock is in a range from 1% to 100%; and the volume concentration of the carrier gas in the feedstock is in a range from 0% to 99%. In the method of the present invention, using a solid acid as a catalyst and ethylene glycol monomethyl ether as a raw material, under a low temperature condition, glycol dimethyl ether and ethylene glycol are prepared directly with high selectivity; moreover, there is substantially or completely no production of by-product 1,4-dioxane that causes pollution to the environment and is harmful to the human body or animal bodies.

7 Claims, No Drawings

METHOD FOR DIRECTLY PREPARING GLYCOL DIMETHYL ETHER AND CO-PRODUCING ETHYLENE GLYCOL FROM ETHYLENE GLYCOL MONOMETHYL ETHER

PRIORITIES AND CROSS REFERENCES

This Application claims priority from International Application No. PCT/CN2015/097160 filed on 11 Dec. 2015 and Chinese Application No. 201510639716.0 filed on 30 Sep. 2015, the teachings of each of which are hereby incorporated by reference in their entirety.

TECHNICAL FIELD

The present invention belongs to the field of chemistry and industrial chemistry, specifically, the present invention refers to a method for directly preparing glycol dimethyl ether and co-producing ethylene glycol from ethylene glycol monomethyl ether.

BACKGROUND

Ethylene glycol dimethyl ether, namely 1,2-dimethoxyethane (DME), is a color less and transparent liquid with an ether smell at normal temperature. It is an aprotic polar solvent with excellent properties, which has a relatively steady nature, and is difficult to participate in a reaction, and is miscible with water and most low carbon (C1-C6) alcohols, ketones and esters at any ratios. It also has a relative strong dissolving capacity to alkali metal compounds. Therefore, it can be the ideal solvent for many organic synthetic reactions. At the same time, it is also widely used as cleaning agent compound, used as additive in textile printing and dyeing, ink painting and fuel. It is also used for synthesizing organic compounds, medical intermediates and the like.

Methods for preparing ethylene glycol dimethyl ether recorded mainly includes: (1) A process of 1,2-dichloroethane reacting with methanol is disclosed in U.S. Pat. No. 3,699,174, in which the metals or metallic oxides of Groups I to V and some transition metals of Groups VI to VIII are respectively used as the catalyst, and the major products are ethylene glycol dimethyl ether and methyl ethyl ether; wherein the percent conversion of the raw material 1,2-dichloroethane is 50% and the selectivity for ethylene glycol dimethyl ether is 24.6%, and the selectivity for dichloromethyl ethyl ether is 46.9%. This process generates many by-products and the yield of the products is not so high; wherein the selectivity for 1,4-dioxane is more than 20%. (2) A process of oxidative coupling reaction of dimethyl ether is disclosed in Japanese patent 60-12089, in which the dimethyl ether is directly oxidized on the surface of the catalyst to obtain ethylene glycol dimethyl ether. However, because that oxygen was added into the reaction system, and dimethyl ether and the product of ethylene glycol dimethyl ether are both flammable substances, there are underlying dangers in this process route. (3) A reaction between dimethyl ether and ethylene oxide is disclosed in U.S. Pat. No. 4,146,736, in which a solid acid catalyst is employed and the percent conversion of the raw material ethylene oxide is nearly 100%, and the selectivity for the product ethylene glycol dimethyl ether is around 65% to 70%, and the selectivity for diethylene glycol dimethyl ether is 15% to 20%, and the sum of the selectivity for tri-, tetra-, pent-ethylene glycol dimethyl ether is around 10%, and the selectivity for 1,4-dioxane is 5% to 7%. However, there are relatively more byproducts in this reaction, and relatively more 1,4-dioxane is generated. (4) Japanese patent 55-104221 has disclosed a method for preparing ethylene glycol dimethyl ether from the dehydration reaction between methanol and ethylene glycol or ethylene glycol monomethyl ether at a reaction temperature of 200□ to 300□; wherein the selectivity for ethylene glycol dimethyl ether in the products is 25%, and the selectivity for diethylene glycol dimethyl ether is 8%, the selectivity for diethylene glycol monomethyl ether is 15%, and there is 1,4-dioxane generated in the process too. (5) U.S. Pat. No. 4,321,413 has disclosed a method for preparing ethylene glycol dimethyl ether at a reaction temperature of 180□ using ethylene glycol monomethyl ether and dimethyl ether as raw materials; wherein the percent conversion of raw material ethylene glycol monomethyl ether is 55.4%, and the selectivity for ethylene glycol dimethyl ether in the product is 62.4%, and the selectivity for 1,4-dioxane is 20% and the selectivity for diethylene glycol dimethyl ether is 16.5%. (6) CN104250206A has disclosed a method for preparing ethylene glycol ether, wherein ethylene glycol and low carbon fatty alcohol are used to prepare ethylene glycol ether in the presence of an acid catalyst, and the solid acid catalyst employed is molecular sieve or zeolite, and the reaction temperature is 20° C. to 250° C., and the reaction pressure is 0.1 MPa to 10 MPa.

In the methods for preparing ethylene glycol dimethyl ether disclosed above, either multiple reactants are employed as the raw materials bring complicated reaction process and complicated by-products, or the reaction condition is too harsh, such as a high reaction temperature. Moreover, there is by-product of 1,4-dioxane existing in all these methods. In addition, when the by-product is dissolved in waste water, it will be hard to be removed using physical separation methods, and the by-product is hard to be biodegraded in nature. At the same time, the by-product may enter human or animal bodies through inhalation, ingestion or skin absorption. When it is cumulated, it will do harm to human or animal bodies because it cannot be metabolic educed.

SUMMARY OF THE INVENTION

To overcome one or all of the above drawbacks, the purpose of the present invention is to provide a method for directly preparing glycol dimethyl ether and co-producing ethylene glycol with a relatively high selectivity in which the starting material is simple, at the same time, there is substantially or completely no production of by-product 1,4-dioxane that causes pollution to the environment and is harmful to the human body or animal bodies generated in the reaction.

Therefore, the present invention provides a method for directly preparing glycol dimethyl ether and co-producing ethylene glycol from ethylene glycol monomethyl ether, which comprises: passing a feedstock containing a raw material of ethylene glycol monomethyl ether and a carrier gas through a reactor loaded with a solid acid catalyst to produce glycol dimethyl ether and ethylene glycol, at a reaction temperature range from 40° C. to 150° C. and a reaction pressure range from 0.1 MPa to 15.0 MPa; wherein a carrier gas is an optional inactive gas; and the feedstock contains water whose volume concentration in the feedstock is in a range from 0% to 95%; and the weight hourly space velocity of the raw material of ethylene glycol monomethyl ether is in a range from 0.05 h$^{-1}$ to 5.0 h$^{-1}$; and the volume concentration of the raw material of ethylene glycol monomethyl ether in the feedstock is in a range from 1% to 100%; and the volume concentration of the carrier gas in the feedstock is in a range from 0% to 99%.

In a preferred embodiment, the water is introduced by being added to the ethylene glycol monomethyl ether.

In a preferred embodiment, the solid acid catalyst is an acidic molecular sieve catalyst or an acidic resin catalyst; preferably, the structure type of the acidic molecular sieve is MWW, FER, MFI, MOR, FAU or BEA.

In a preferred embodiment, the acidic molecular sieve is one or more molecular sieves selected from the group consisting of MCM-22 molecular sieve, ferrierite molecular sieve, ZSM-5 molecular sieve, mordenite molecular sieve, Y molecular sieve and β molecular sieve.

In a preferred embodiment, the atom ratio of Si to Al in the MCM-22 molecular sieve Si/Al is in a range from 5 to 100; the atom ratio of Si to Al in the ferrierite molecular sieve Si/Al is in a range from 5 to 100; the atom ratio of Si to Al in the ZSM-5 molecular sieve Si/Al is in a range from 5 to 100; the atom ratio of Si to Al in the mordenite molecular sieve Si/Al is in a range from 5 to 50; the atom ratio of Si to Al in the Y zeolite molecular sieve Si/Al is in a range from 3 to 50; and the atom ratio of Si to Al in the β molecular sieve Si/Al is in a range from 5 to 100.

In a preferred embodiment, the acidic molecular sieve catalyst comprises one or more metals selected from the group consisting of alkali metal, alkaline earth metal and rare earth metal; and the mass fraction of the metal is in a range from 0.1% to 10%; preferably, the mass fraction of the metal is in a range from 0.1% to 4%; and the acidic molecular sieve catalyst comprises one or more binders selected from the group consisting of aluminium oxide and silicon oxide, and the mass fraction of the binder is in a range from 1% to 40%.

In a preferred embodiment, the acidic resin catalyst is one or more resins selected from the group consisting of benzenesulfonic acid resin, para-toluenesulfonic acid resin, perfluorosulfonic acid resin and strong acidic cation exchange resin; preferably, the acidic resin catalyst is perfluorosulfonic acid resin Nafion.

In a preferred embodiment, the reaction temperature is in a range from 50° C. to 150° C., and the reaction pressure is in a range from 3.0 MPa to 8.0 MPa, and the weight hourly space velocity of the raw material of ethylene glycol monomethyl ether is in a range from 0.3 h$^{-1}$ to 2.0 h$^{-1}$.

In a preferred embodiment, the inactive gas is one or more gases selected from the group consisting of nitrogen, helium and argon, and the volume concentration of the carrier gas in the feedstock is in a range from 1% to 99%.

In a preferred embodiment, the reactor is a fixed bed reactor or a tank reactor.

In the method of the present invention, using a solid acid as a catalyst and ethylene glycol monomethyl ether as a raw material, under a low temperature condition, glycol dimethyl ether and ethylene glycol are prepared directly with high selectivity. The product is simple and there are less side reactions existing in the method, and the selectivity for the target products of ethylene glycol dimethyl ether and ethylene glycol can reach 50% of the theoretical value. Moreover, there is substantially or completely no production of by-product 1,4-dioxane that causes pollution to the environment and is harmful to the human body or animal bodies.

DETAILED DESCRIPTION OF THE EMBODIMENT

The present application provides a method for directly and efficiently preparing glycol dimethyl ether and co-producing ethylene glycol from ethylene glycol monomethyl ether under a low temperature condition on a solid acid catalyst. More specifically, the method of the present invention comprises passing a feedstock containing a raw material of ethylene glycol monomethyl ether and a carrier gas through a reactor loaded with a solid acid catalyst to produce glycol dimethyl ether and ethylene glycol, at a reaction temperature range from 40° C. to 150° C. and a reaction pressure range from 0.1 MPa to 15.0 MPa; wherein a carrier gas is an optional inactive gas; and the feedstock contains water whose volume concentration in the feedstock is in a range from 0% to 95%; and the weight hourly space velocity of the raw material of ethylene glycol monomethyl ether is in a range from 0.05 h-1 to 5.0 h-1; and the volume concentration of the raw material of ethylene glycol monomethyl ether in the feedstock is in a range from 1% to 100%; and the volume concentration of the carrier gas in the feedstock is in a range from 0% to 99%.

In the present invention, unless otherwise specified, all of the above mentioned volume concentrations of the raw material of ethylene glycol monomethyl ether, the carrier gas and the water are based on their total volume existing in the reaction system. For example, when there is only the raw material of ethylene glycol monomethyl ether existing in the reaction system, the volume concentration of the ethylene glycol monomethyl ether shall be 100%; while when there are the raw material of ethylene glycol monomethyl ether and the carrier gas existing in the reaction system, each volume concentration of them is based on the total volume of ethylene glycol monomethyl ether and the carrier gas; and when there are the raw material of ethylene glycol monomethyl ether, carrier gas and water existing in the reaction system, each volume concentration of them is based on the total volume of ethylene glycol monomethyl ether, carrier gas and water.

In the present invention, the feeding manners of the raw material of ethylene glycol monomethyl ether may be listed as follows:

The first manner is that when there is no a carrier gas existing, the raw material of ethylene glycol monomethyl ether in liquid state is directly pumped into the reactor, such as a fixed bed reactor, using a feeding pump, such as a constant flow pump, at a certain flow rate, such as a flow rate in a range from 0.1 mL/min to 10 mL/min, to realize the feeding process.

The second manner is that when there is a carrier gas existing, the saturated vapor of ethylene glycol monomethyl ether is carried by an inactive gas acting as the carrier gas, such as $N_2$, into a fixed bed reactor, at different water-bath temperatures (40-80□). Preferably, the flow rate of the carrier gas is in a range from 10 mL/min to 50 mL/min. The mole of the raw material of ethylene glycol monomethyl ether entering the reactor in unit time can be calculated from the saturated vapor pressure and the $N_2$ flow rate. The calculating method of the saturated vapor pressure of the raw material of ethylene glycol dimethyl ether at different temperatures is shown as follows, $$\ln(p_1^*/p_2^*) = -\Delta VapHm/8.3145 \times (1/T_1 - 1/T_2)$$

wherein, $p_1^*$ and $p_2^*$ respectively represents the saturated vapor pressures of the raw material of ethylene glycol dimethyl ether at different temperatures; ΔVapHm represents the molar enthalpy of vaporization of ethylene glycol monomethyl ether (39.48 KJ/mol); $T_1$ and $T_2$ respectively represent the different temperatures (the unit is K); the saturated vapor pressure at 253K is 3.968 kPa, and thus the saturated vapor pressure of the raw material of ethylene glycol dimethyl ether at any temperature can be calculated.

Preferably, the solid acid catalyst employed in the present invention is acidic molecular sieve catalyst or acidic resin catalyst; more preferably, the structure type of the acidic molecular sieve is MWW, FER, MFI, MOR, FAU or BEA.

Furthermore preferably, the acidic molecular sieve employed in the present invention is one or more molecular sieves selected from the group consisting of MCM-22 molecular sieve, ferrierite molecular sieve, ZSM-5 molecular sieve, mordenite molecular sieve, Y molecular sieve and β molecular sieve.

Preferably, in the present invention, the atom ratio of Si to Al in the MCM-22 molecular sieve Si/Al is in a range from 5 to 100; the atom ratio of Si to Al in the ferrierite molecular sieve Si/Al is in a range from 5 to 100; the atom ratio of Si to Al in the ZSM-5 molecular sieve Si/Al is in a range from 5 to 100; the atom ratio of Si to Al in the mordenite molecular sieve Si/Al is in a range from 5 to 50; the atom ratio of Si to Al in the Y molecular sieve Si/Al is in a range from 3 to 50; and the atom ratio of Si to Al in the β molecular sieve Si/Al is in a range from 5 to 100.

Preferably, in the present invention, the acidic resin catalyst may be any resin containing sulfonic acid functional group, such as benzenesulfonic acid resin, para-toluenesulfonic acid resin, perfluorosulfonic acid resin; more preferably, the acidic resin catalyst is one or more resins selected from the group consisting of perfluorosulfonic acid resin Nafion and strong acidic cation exchange resin.

Preferably, in the present invention, the reaction temperature is in a range from 50° C. to 150° C.; more preferably the reaction temperature is in a range from 80° C. to 150° C.; and the reaction pressure is in a range from 3 MPa to 8 MPa, and the weight hourly space velocity of the raw material of ethylene glycol monomethyl ether is in a range from 0.3 h$^{-1}$ to 2.0 h$^{-1}$.

Preferably, in the present invention, the carrier gas is one gas or a mixed gas containing more gases selected from the group consisting of nitrogen, helium and argon; more preferably, the weight hourly space velocity of the carrier gas is in a range from 50.0 h$^{-1}$ to 12000.0 h$^{-1}$, and further more preferably, the weight hourly space velocity of the carrier gas is in a range from 600.0 h$^{-1}$ to 5000.0 h$^{-1}$.

Preferably, in the present invention, the reactor is a fixed bed reactor or a tank reactor, which can realize continuous reaction; preferably, the reactor is a fixed bed reactor.

Without being limited by any theory, in the reactions of the present invention, chemical reactions of the raw material of ethylene glycol monomethyl ether that may occur on the surface of the catalyst are shown as the following Formulas I to IX:

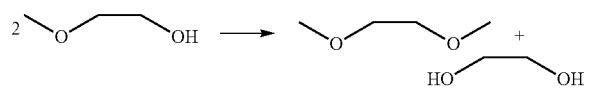

Formula I

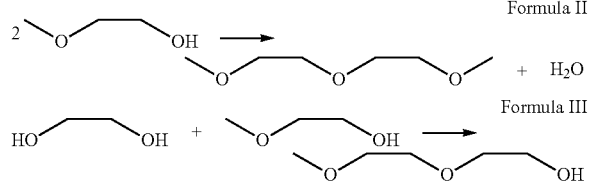

Formula II

Formula III

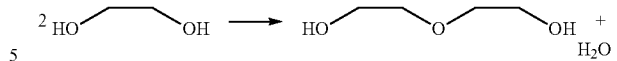

Formula IV

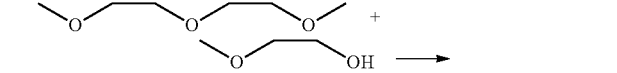

Formula V

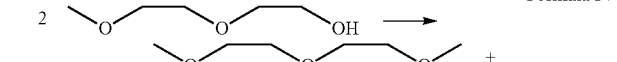

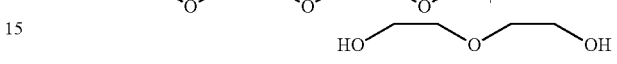

Formula IV

Formula VII

Formula VIII

Formula IX

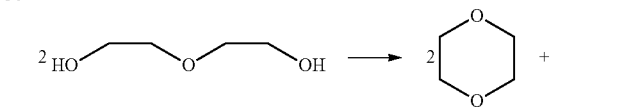

Specifically, when at a relatively lower reaction temperature, as shown in Formula I, a self-disproportionation reaction occurs by a great quantity of the raw material of ethylene glycol monomethyl ether, generating ethylene glycol dimethyl ether and ethylene glycol; and meanwhile, as shown in Formula II, an intermolecular dehydration also may occur by the raw material of ethylene glycol monomethyl ether, generating diethylene glycol dimethyl ether and water with a molar ratio of 1:1.

With the reaction temperature gradually increasing, as shown in Formula III and Formula IV, an intermolecular dehydration occurs by the generated ethylene glycol and the raw material of ethylene glycol monomethyl ether, generating diethylene glycol monomethyl ether; meanwhile a self-dehydration may occur by a small quantity of ethylene glycol, generating diethylene glycol. Moreover, as shown in Formula V, a transetherification reaction occurs by the generated diethylene glycol dimethyl ether and the raw material of ethylene glycol monomethyl ether, generating diethylene glycol monomethyl ether and ethylene glycol dimethyl ether. While as shown in Formula VI, a self-disproportionation reaction may occur by the generated diethylene glycol monomethyl ether, generating diethylene glycol dimethyl ether and diethylene glycol.

However, with the reaction temperature further increasing, as shown in Formulas VII to IX, a intramolecular dehydration occurs by the generated diethylene glycol dimethyl ether, diethylene glycol monomethyl ether and diethylene glycol, generating 1,4-dioxane and bring a great rise of the selectivity for by-product 1,4-dioxane.

Therefore, it can be seen from the above reaction processes that, the reaction products that may be obtained from the raw material of ethylene glycol monomethyl ether are ethylene glycol dimethyl ether, ethylene glycol, diethylene glycol monomethyl ether, water, diethylene glycol dimethyl ether, diethylene glycol and 1,4-dioxane, and a very small amount of methanol and dimethyl ether.

For the present invention, it is ideal that only the reaction shown in Formula I occurs, namely only ethylene glycol dimethyl ether and ethylene glycol are generated. For this purpose, the inventors of the present invention went into an intensive study and discovered that, controlling the temperature to be in a range of 40° C. to 150° C. is very crucial to make only the reactions of Formula I and Formula II occur. Because when the temperature is below than 40° C., the reaction cannot occur or occurs in a very low reaction rate, and the yield of the target product is relatively low; while when the reaction temperature is over 150° C., the reactions of Formula III to Formula VII increase, which causes the increase of the by-products, and especially causes the generation of a large amount of by-product 1,4-dioxane. On the other hand, for the purpose of reducing the reaction shown in Formula II, the presence of water in the reaction system of the present invention may be preferred, which can be seen from the equilibrium of reaction. Because water is a product of the reaction of Formula II, when water is pre-existing, the reaction of Formula II shall be inhibited or reduced. The water can be introduced by being added to the raw material of ethylene glycol monomethyl ether or being carried by the carrier gas, or may exist in the reactor itself.

In the present invention, the products were detected and identified by gas chromatography analysis. Therefore, "substantially or completely no production of by-product 1,4-dioxane" in this text means that 1,4-dioxane exists at an amount which cannot be detected by the above mentioned gas chromatography.

EXAMPLES

The present invention is further illustrated in combination with specific Examples as follows. It should be understood that, these Examples are only used for illustrate the present invention but not to limited the scope thereof.

Unless otherwise specified, the raw materials and catalysts employed in the Examples of the present invention are commercial purchased and directly used.

Analytic method in the Examples is listed as follows:

The raw material and the products are both detected by gas chromatography Agilent 7890 equipped with a 50 meter HP-FFAP capillary column.

In the Examples and Comparative Examples of the present invention, the reaction conditions are as follows:

Using a fix bed reactor, the loading mass of the catalyst is in a range from 1 g to 10 g, and the reaction temperature is in a range from 40° C. to 250° C. (wherein the temperatures higher than 150° C. are used in the Comparative Examples of the present invention), and the reaction pressure is in a range from 0.1 MPa to 10 MPa; raw material of ethylene glycol monomethyl ether enters the reactor through two manners.

Example 1

H-β molecular sieve (Si/Al=16) was pressed under a pressure of 40 MPa, then crushed and sieved to 20-40 mesh to obtain a catalyst for use. 1 g of the catalyst was loaded into the fixed bed reactor and pretreated. The pretreatment conditions of the catalyst are listed as follows: the flow rate of $N_2$ was 30 ml/min, and the temperature was raised from 25° C. to 500° C. in 150 min, and then kept at 500° C. for 180 min.

The raw material of ethylene glycol monomethyl ether was carried into the reactor by $N_2$ at a water-bath temperature of 60° C.; wherein the flow rate of $N_2$ was 30 ml/min, and the reaction pressure was 0.5 MPa.

The variations of percent conversion of the raw materials and the selectivity for the products with temperature are shown in Table 1.

TABLE 1

Reactivity of raw material of ethylene glycol monomethyl ether and the selectivity for the products at different temperatures on the H-β molecular sieve catalyst.

| Reaction temperature (° C.) | Percentage Conversion (%) Ethylene glycol monomethyl ether | Selectivity (%) | | | | | | |
|---|---|---|---|---|---|---|---|---|---|
| | | Dimethyl ether | Methanol | Ethylene glycol dimethyl ether | Ethylene glycol | 1,4-dioxane | Diethylene glycol | Diethylene glycol dimethyl ether | Diethylene glycol monomethyl ether |
| 40 | 6 | 0 | 0 | 50 | 50 | 0 | 0 | 0 | 0 |
| 50 | 12 | 0 | 0 | 50 | 50 | 0 | 0 | 0 | 0 |
| 70 | 19 | 0 | 0 | 50 | 50 | 0 | 0 | 0 | 0 |
| 90 | 38 | 0 | 0.1 | 50 | 30 | 0 | 6 | 4.6 | 9.4 |
| 110 | 59 | 0.1 | 0.2 | 50 | 20 | 0 | 12 | 4.2 | 13.8 |
| 120 | 68 | 0.1 | 0.3 | 50 | 6.1 | 0 | 20 | 3.5 | 18 |
| 130 | 72 | 0.5 | 1 | 50 | 2.8 | 0 | 17.9 | 3.1 | 18.7 |
| 140 | 92 | 1 | 1 | 50 | 2 | 0 | 14.1 | 1.9 | 18 |
| 150 | 100 | 9 | 2 | 50 | 0.6 | 0 | 2.1 | 0.2 | 3.1 |
| 170 | 100 | 31 | 3 | 4 | 0 | 62 | 0 | 0 | 0 |
| 190 | 100 | 32 | 3 | 0 | 0 | 65 | 0 | 0 | 0 |
| 220 | 100 | 34 | 0 | 0 | 0 | 66 | 0 | 0 | 0 |
| 250 | 100 | 34 | 0 | 0 | 0 | 66 | 0 | 0 | 0 |

Reaction conditions: reaction pressure is 0.5 MPa, mass of the catalyst is 1 g, water bath temperature It can be seen from Table 1 that, when using a H-β molecular with a Si to Al ratio of 16 as the catalyst, with the reaction temperature rising from 40° C. to 150° C., the percent conversion of the raw material of ethylene glycol monomethyl ether increases gradually, and when the temperature reaches 150° C., the percent conversion of the raw material can reach 100%; and when the reaction temperature is below than 150° C., there is no 1,4-dioxane generated in the products. When the reaction temperature is in a relatively low range from 50° C. to 80° C., a self-disproportionation reaction mainly occurs by the raw material, generating ethylene glycol dimethyl ether and diethylene glycol; when the reaction temperature is in a range from 90° C. to 150° C., the ethylene glycol may react with the raw material of ethylene glycol monomethyl ether by a dehydration reaction, generating diethylene glycol monomethyl ether, or a self-dehydration reaction may occur by ethylene glycol, generating diethylene glycol. When the reaction temperature is over 150° C., although the percent conversion of the raw material is still kept at 100%, the reactions in the above mentioned Formula III to Formula IX increase, and thus the reaction products are dimethyl ether, methanol, ethylene glycol, 1,4-dioxane, diethylene glycol, diethylene glycol dimethyl ether and diethylene glycol monomethyl ether; wherein the selectivity for 1,4-dioxane raises sharply due to an intramolecular dehydration occurs respectively in diethylene glycol monomethyl ether molecules and diethylene glycol molecules, generating 1,4-dioxane. It can be seen from Table 1 that, using a H-β molecular with a Si to Al ratio of 16 as the catalyst, at the reaction temperature range and reaction pressure range in the present invention, the selectivity for ethylene glycol dimethyl ether is 50% and the selectivity for ethylene glycol is in a range from 0.6% to 50%, and there is no 1,4-dioxane generated at all.

Example 2

H-Y molecular sieve (Si/Al=10.6) was pressed under a pressure of 40 MPa, then crushed and sieved to 20-40 mesh to obtain a catalyst for use. 1 g of the catalyst was loaded into the fixed bed reactor and pretreated. The pretreatment conditions are listed as follows: the flow rate of $N_2$ was 30 ml/min, and the temperature was raised from 25° C. to 500° C. in 150 min, and then kept at 500° C. for 180 min.

The raw material of ethylene glycol monomethyl ether was carried into the reactor by $N_2$ at a water-bath temperature of 60° C.; wherein the flow rate of $N_2$ was 30 ml/min, and the reaction pressure was 0.5 MPa.

The variations of percent conversion of the raw materials and the selectivity of the products with temperature are shown in Table 2.

Reaction conditions: reaction pressure is 0.5 MPa, mass of the catalyst is 1 g, water bath temperature is 60° C., flow rate of $N_2$ is 30 mL/min.

It can be seen from Table 2 that, using a H-β molecular having a Si to Al ratio of 16 as the catalyst, when the reaction temperature is below than 150° C., the percent conversion of the raw material ethylene glycol monomethyl ether is lower than 10% and the major products are ethylene glycol dimethyl ether and ethylene glycol, indicating that when the reaction temperature is in a relatively low range from 80° C. to 120° C., the raw material mainly occurred a self-disproportionation reaction mainly occurs by the raw material. When the reaction temperature is in a range from 120° C. to 150° C., the ethylene glycol can react with raw material ethylene glycol monomethyl ether by a dehydration reaction, generating diethylene glycol monomethyl ether, or that a self-dehydration reaction may occur by ethylene glycol, generating diethylene glycol, causing the selectivities for ethylene glycol monomethyl ether and diethylene glycol in the products increased. However, when the reaction temperature is over 170° C., although the percent conversion of the raw material increases, for example, the percent conversion of the raw material can reach 80% at 200° C., the selectivity for ethylene glycol dimethyl ether in the products decreases sharply and the selectivities for dimethyl ether and 1,4-dioxane increase significantly. When the reaction temperature is 230° C., the selectivity for dimethyl ether is 18% and the selectivity for 1,4-dioxane is 65%. It can be seen from Table 2 that, using a H-Y molecular having a Si to Al ratio of 10.6 as the catalyst, at the reaction temperature range and reaction pressure range in the present invention, the selectivity for the ethylene glycol dimethyl ether is 50% and the selectivity for ethylene glycol is in a range from 22% to 48%, and there is no 1,4-dioxane generated at all.

Example 3

H-β, H-Y, H-ZSM-5, H-MOR, F-FER molecular sieves with different Si to Al ratios respectively were pressed under a pressure of 40 MPa, then crushed and sieved to 20-40 mesh to obtain catalysts for use. 1 g of each catalyst was respectively loaded into the fixed bed reactors and pretreated. The pretreatment conditions are listed as follows: the flow rate of $N_2$ was 30 ml/min, and the temperature was raised from 25° C. to 500° C. in 150 min, and then kept at 500° C. for 180 min. The raw material of ethylene glycol monomethyl ether was carried into the reactor by $N_2$ at a water-bath temperature of 60° C.; wherein the flow rate of $N_2$ was 30 ml/min. Space velocity, reaction pressure.

TABLE 2

Reactivity of raw material ethylene glycol monomethyl ether and the selectivity of the products at different temperatures on the H-Y molecular sieve catalyst.

| | Percentage Conversion (%) | Selectivity (%) | | | | | | | |
|---|---|---|---|---|---|---|---|---|---|
| Reaction temperature (° C.) | Ethylene glycol monomethyl ether | Dimethyl ether | Methanol | Ethylene glycol dimethyl ether | Ethylene glycol | 1,4-dioxane | Diethylene glycol | Diethylene glycol dimethyl ether | Diethylene glycol monomethyl ether |
| 80 | 2 | 0 | 0 | 50 | 50 | 0 | 0 | 0 | 0 |
| 110 | 3 | 0 | 0 | 50 | 48 | 0 | 0 | 0 | 2 |
| 120 | 6 | 0 | 0 | 50 | 40 | 0 | 4 | 0 | 6 |
| 150 | 10 | 0 | 0 | 50 | 22 | 0 | 10 | 0 | 13 |
| 170 | 30 | 3 | 1 | 49 | 3 | 20 | 11 | 0 | 13 |
| 200 | 80 | 12 | 2 | 31 | 0 | 55 | 0 | 0 | 0 |
| 230 | 95 | 18 | 3 | 14 | 0 | 65 | 0 | 0 | 0 |

The variations of percent conversion of the raw materials and the selectivity for the products of ethylene glycol dimethyl ether and 1,4-dioxane with temperature are shown in Table 3.

TABLE 3

Reactivity of ethylene glycol monomethyl ether on molecular sieve catalysts with different topological structures and different Si to Al ratios, and the selectivity for the products of ethylene glycol dimethyl ether and 1,4-dioxane at different temperatures and different reaction pressure. (This table merely shows the selectivity for the major products, and the data of other products are not shown).

| Catalyst type | Si/Al | Reaction temperature (° C.) | Reaction pressure (Mpa) | Percentage conversion (%) Ethylene glycol monomethyl ether | Selectivity (%) Ethylene glycol dimethyl ether | 1,4-dioxane | Ehylene glycol |
|---|---|---|---|---|---|---|---|
| H-β | 5 | 130 | 0.5 | 42 | 50 | 0 | 3 |
| H-β | 100 | 130 | 0.5 | 94 | 50 | 0 | 2.5 |
| H-β | 30 | 130 | 5 | 86 | 56 | 0 | 2.6 |
| H-β | 50 | 120 | 10 | 87 | 60 | 0 | 3.2 |
| H-Y | 5 | 150 | 0.5 | 3 | 49 | 0 | 22 |
| H-Y | 50 | 150 | 6 | 50 | 54 | 0 | 24 |
| H-ZSM-5 | 25 | 110 | 1 | 44 | 46 | 0 | 20 |
| H-ZSM-5 | 50 | 110 | 1 | 67 | 32 | 0 | 22 |
| H-MOR | 14 | 140 | 6 | 39 | 48 | 0 | 25 |
| H-MOR | 30 | 140 | 6 | 48 | 42 | 0 | 25 |
| H-FER | 5 | 150 | 9 | 8 | 54 | 0 | 21 |
| H-FER | 20 | 150 | 9 | 12 | 52 | 0 | 21 |

Reaction conditions: mass of the catalyst is 1 g, water bath temperature is 60° C., flow rate of $N_2$ is 30 mL/min.

It can be seen from Table 3 that, all those molecular sieves with different Si to Al ratios, i.e. H-β, H-Y, H-ZSM-5, H-MOR, F-FER molecular sieves, possess catalytic activity at the reaction temperature range and reaction pressure range in the present invention, and, and there is no 1,4-dioxane generated.

Example 4

0.5 g of perfluorosulfonic acid resin (Nafion-H) was loaded into a fixed bed reactor and pretreated. The pretreatment conditions are listed as follows: the flow rate of $N_2$ was 30 ml/min, and the temperature was raised from 25° C. to 150° C. in 60 min, and then kept at 150° C. for 180 min. The raw material of ethylene glycol monomethyl ether was carried into the reactor by $N_2$ at a water-bath temperature of 60° C.; wherein the flow rate of $N_2$ was 30 ml/min, and the reaction pressure was 0.5 MPa.

The variations of percent conversion of the raw materials and the selectivity of the products with temperature are shown in Table 4.

TABLE 4

Reactivity of raw material ethylene glycol monomethyl ether and the selectivity for the products at different temperatures on the Nafion-H catalyst. (This table merely shows the selectivity for the major products, and the data of other relevant products are not shown).

| Reaction temperature (° C.) | Percentage Conversion (%) Ethylene glycol monomethyl ether | Selectivity (%) Dimethyl ether | Methanol | Ethylene glycol dimethyl ether | Ethylene glycol | 1,4-dioxane | Diethylene glycol | Diethylene glycol dimethyl ether | Diethylene glycol monomethyl ether |
|---|---|---|---|---|---|---|---|---|---|
| 50 | 8 | 0.1 | 0 | 15 | 2 | 0 | 8 | 55 | 14 |
| 60 | 20 | 0.1 | 0 | 15 | 3 | 0 | 8 | 52 | 14 |
| 80 | 45 | 0.1 | 0 | 14 | 4 | 0 | 8 | 50 | 14 |
| 100 | 66 | 1 | 0 | 14 | 3 | 0 | 10 | 40 | 13 |
| 120 | 88 | 4 | 0 | 10 | 3 | 0 | 10 | 34 | 14 |
| 140 | 95 | 6 | 0 | 8 | 2 | 0 | 10 | 32 | 13 |
| 150 | 100 | 8 | 0 | 3 | 3 | 0 | 8 | 28 | 11 |

Reaction conditions: reaction pressure is 0.5 MPa, mass of the catalyst is 0.5 g, water bath temperature is 60° C., flow rate of $N_2$ is 30 mL/min.

Example 5

Benzenesulfonic acid resin, para-toluenesulfonic acid resin solid and perfluorosulfonic acid resin (Nafion-H) with different masses were loaded into a fixed bed reactor and pretreated. The pretreatment conditions are listed as follows: the flow rate of $N_2$ was 30 ml/min, and the temperature was raised from 60° C. to 130° C. in 60 min, and then kept at 150° C. for 180 min.

The raw material of ethylene glycol monomethyl ether was carried into the reactor by $N_2$ at a water-bath temperature of 60° C.; wherein the flow rate of $N_2$ was 30 ml/min.

The variations of percent conversion of the raw materials and the selectivity for the products with reaction temperature and reaction pressure are shown in Table 5.

TABLE 5

Reactivity of raw material of ethylene glycol monomethyl ether and the selectivity for the products ethylene glycol dimethyl ether and 1,4-dioxane at different temperatures and different reaction pressure on resin catalysts with different masses. (This table merely shows the selectivity for the major products, and the data of other relevant products are not shown).

| Catalyst type | Mass of the Catalyst (g) | Reaction temperature (° C.) | Reaction pressure (Mpa) | Percentage conversion (%) Ethylene glycol monomethyl ether | Selectivity (%) Ethylene glycol dimethyl ether | 1,4-dioxane | Ethylene glycol |
|---|---|---|---|---|---|---|---|
| perfluorosulfonic acid resin | 1 | 60 | 0.5 | 30 | 16 | 0 | 2.5 |
| perfluorosulfonic acid resin | 3 | 60 | 5 | 52 | 24 | 0 | 2.7 |
| perfluorosulfonic acid resin | 2 | 60 | 10 | 47 | 23 | 0 | 2.9 |
| benzenesulfonic acid resin | 1 | 80 | 0.5 | 25 | 39 | 0 | 2.2 |
| benzenesulfonic acid resin | 1 | 80 | 3 | 31 | 40 | 0 | 2.4 |
| benzenesulfonic acid resin | 1 | 100 | 1 | 52 | 43 | 0 | 2.6 |
| benzenesulfonic acid resin | 1 | 130 | 1 | 74 | 32 | 0 | 2.8 |
| para-toluenesulfonic acid resin | 1 | 80 | 0.5 | 41 | 42 | 0 | 2.4 |
| para-toluenesulfonic acid resin | 1 | 80 | 4 | 47 | 46 | 0 | 2.5 |
| para-toluenesulfonic acid resin | 1 | 100 | 1 | 61 | 43 | 0 | 2.5 |
| para-toluenesulfonic acid resin | 1 | 130 | 1 | 80 | 39 | 0 | 2.4 |

Reaction conditions: water bath temperature is 60° C., flow rate of $N_2$ is 30 mL/min.

It can be seen from Table 5 that, using perfluorosulfonic acid resin, benzenesulfonic acid resin and para-toluenesulfonic acid resin solid as the catalysts, at the reaction temperature range and reaction pressure range in the present invention, the selectivity for ethylene glycol dimethyl ether is in a range from 16% to 46% and the selectivity for ethylene glycol is around 2.5%, and there is no 1,4-dioxane generated at all.

Example 6

H-β molecular sieve (Si/Al=10.6, the topological structure is H-BEA) was pressed under a pressure of 40 MPa, then crushed and sieved to 20-40 mesh to obtain a catalyst for use. 3 g of each catalyst was loaded into a fixed bed reactor and pretreated. The pretreatment conditions are listed as follows: the flow rate of $N_2$ was 30 ml/min, and the temperature was raised from 25° C. to 500° C. in 150 min, and then kept at 500° C. for 180 min.

The raw material ethylene of glycol dimethyl ether was pumped into the reactor by a micro constant flow pump; wherein the flow rate was 0.03 mL/min, and the weight hourly space velocity was 0.6 $h^{-1}$, and the reaction pressure was 0.1 MPa.

The variations of percent conversion of the raw materials and the selectivity for the products with temperature are shown in Table 6.

TABLE 6

Reactivity of raw material of ethylene glycol monomethyl ether and the selectivity for the products at different temperatures on the H-β catalyst (This table merely shows the selectivities for the major products, and the data of other relevant products are not shown).

| Reaction temperature (° C.) | Percentage Conversion (%) Ethylene glycol monomethyl ether | Selectivity (%) Dimethyl ether | Methanol | Ethylene glycol dimethyl ether | Ethylene glycol | 1,4-dioxane | Diethylene glycol | Diethylene glycol dimethyl ether | Diethylene glycol monomethyl ether |
|---|---|---|---|---|---|---|---|---|---|
| 110 | 8 | 0 | 0 | 50 | 22 | 0 | 5 | 3 | 20 |
| 120 | 20 | 0.1 | 0.18 | 50 | 6.6 | 0 | 13 | 4.52 | 18 |
| 150 | 49 | 0.3 | 0.15 | 50 | 2.5 | 0 | 1.99 | 0.2 | 2.76 |

Reaction conditions: reaction pressure was 0.1 MPa, space velocity was 0.6 h$^{-1}$, flow rate of N$_2$ was 50 mL/min.

It can be seen from Table 6 there is no 1,4-dioxane generated at all at the reaction temperature in a range from 110° C. to 150° C. And with the reaction temperature rising, the percent conversion of raw material is significantly enhanced; and at the reaction temperature of 150° C., the percent conversion of raw material can reach 49% and the selectivity for ethylene glycol dimethyl ether in the products is 52%. When the reaction temperature rising to 180° C., although the percent conversion of raw material is further enhanced, the selectivity for 1,4-dioxane also increases significantly.

Example 7

Using the same catalyst, pretreatment conditions and manner of feedstock being introduced into the reactor as in Example 6, and the volume ratios of the raw material of ethylene glycol monomethyl ether to water respectively were 1:0.01, 1:0.1, 1:1, 1:4 and 1:10 (the volume concentrations of water respectively were 0.99%, 9.09%, 50.00%, 80.00% and 90.91%), and the weight hourly space velocity was 3.0 h$^{-1}$.

The variations of percent conversion of the raw materials and the selectivity for the products with temperature are shown in Table 7.

TABLE 7

Reactivity of raw material of ethylene glycol monomethyl ether and the selectivity for the products at 110° C. on the H-β catalyst (This table merely shows the selectivity for the major products, and the data of other relevant products are not shown).

| Reaction temperature (° C.) | Percentage Conversion (%) Ethylene glycol monomethyl ether | Selectivity (%) | | | | | | | |
|---|---|---|---|---|---|---|---|---|---|
| | | Dimethyl ether | Ethylene glycol monomethyl ether | Dimethyl ether | Ethylene glycol monomethyl ether | Dimethyl ether | Ethylene glycol monomethyl ether | Dimethyl ether | Ethylene glycol monomethyl ether |
| 110 | 49 | 0.2 | 0.1 | 50 | 4.5 | 0 | 2.4 | 0.1 | 2.6 |
| 110 | 50 | 0.1 | 0 | 50 | 6 | 0 | 4.3 | 0.1 | 4.5 |
| 110 | 50 | 0 | 0 | 50 | 18 | 0 | 7 | 0 | 9 |
| 110 | 52 | 0 | 0 | 50 | 20 | 0 | 9 | 0 | 12 |
| 110 | 52 | 0 | 0 | 50 | 22 | 0 | 10 | 0 | 12 |

It can be seen from Table 7 that, when the reaction temperature is 110° C., the addition of water in the raw material significantly reduces the selectivity for diethylene glycol and diethylene glycol dimethyl ether in the products.

The above said are only several Examples of the present application, and they do not limit the scope of the present application. Though the present application is disclosed with relatively preferred Examples above, it does not means that the present application is limited by them. Any variations and optimizations made by the skilled in the art who is familiar with this major utilizing the above disclosed technical methods are all equal to the equivalent embodiments of the present application which is included in the scope of the technical methods of the present application.

The invention claimed is:

1. A method for directly preparing glycol dimethyl ether and co-producing ethylene glycol from ethylene glycol monomethyl ether, which comprises: passing a feedstock containing a raw material of ethylene glycol monomethyl ether and a carrier gas through a reactor loaded with a solid acid catalyst to produce glycol dimethyl ether and ethylene glycol, at a reaction temperature range from 40° C. to 150° C. and a reaction pressure range from 0.1 MPa to 15.0 MPa; wherein a carrier gas is an optional inactive gas; and the feedstock contains water whose volume concentration in the feedstock is no more than 95%; and the weight hourly space velocity of the raw material of ethylene glycol monomethyl ether is in a range from 0.05 h$^{-1}$ to 5.0 h$^{-1}$; and the volume concentration of the raw material of ethylene glycol monomethyl ether in the feedstock is in a range from 1% to 100%; and the volume concentration of the carrier gas in the feedstock is no more than 99%, wherein the volume concentration of all components of the feedstock is 100%; and
   wherein the solid acid catalyst is an acidic molecular sieve catalyst; and
   wherein the acidic molecular sieve catalyst is one or more molecular sieves selected from the group consisting of an MCM-22 molecular sieve, a ferrierite molecular sieve, a ZSM-5 molecular sieve, a mordenite molecular sieve, a Y molecular sieve and a β molecular sieve; wherein
   the atom ratio of Si to Al in the MCM-22 molecular sieve Si/Al is in a range from 5 to 100;
   the atom ratio of Si to Al in the ferrierite molecular sieve Si/Al is in a range from 5 to 100;
   the atom ratio of Si to Al in the ZSM-5 molecular sieve Si/Al is in a range from 5 to 100;
   the atom ratio of Si to Al in the mordenite molecular sieve Si/Al is in a range from 5 to 50;
   the atom ratio of Si to Al in the Y molecular sieve Si/Al is in a range from 3 to 50; and the atom ratio of Si to Al in the β molecular sieve Si/Al is in a range from 5 to 100.

2. The method according to claim 1, wherein the water is introduced by being added to the raw material of ethylene glycol monomethyl ether.

3. The method according to claim 1, wherein the acidic molecular sieve catalyst comprises one or more metals selected from the group consisting of alkali metal, alkaline earth metal and rare earth metal; and the mass fraction of the metal is in a range from 0.1% to 10%.

4. The method according to claim 1, wherein the reaction temperature is in a range from 50° C. to 150° C., and the reaction pressure is in a range from 3.0 MPa to 8.0 MPa, and the weight hourly space velocity of the raw material of ethylene glycol monomethyl ether is in a range from 0.3 h$^{-1}$ to 2.0 h$^{-1}$.

5. The method according to claim 1, wherein the inactive gas is one or more gases selected from the group consisting of nitrogen, helium and argon, and the volume concentration of the carrier gas in the feedstock is in a range from 1% to 99%.

6. The method according to claim 1, wherein the reactor is a fixed bed reactor or a tank reactor.

7. The method according to claim 3, wherein a mass fraction of the metal is in a range from 0.1% to 4%; and the acidic molecular sieve catalyst comprises one or more binders selected from the group consisting of aluminium oxide and silicon oxide; and the mass fraction of the binder is in a range from 1% to 40%.

* * * * *